United States Patent
Weber

(10) Patent No.: US 9,670,044 B2
(45) Date of Patent: Jun. 6, 2017

(54) SAMPLE PREPARATION SYSTEM WITH ROTATABLE GRIPPER

(71) Applicant: Mettler-Toledo AG, Greifensee (CH)

(72) Inventor: René Weber, Esslingen (CH)

(73) Assignee: Mettler-Toledo GmbH, Greifensee (CH)

( * ) Notice: Subject to any disclaimer, the term of this patent is extended or adjusted under 35 U.S.C. 154(b) by 514 days.

(21) Appl. No.: 14/254,168

(22) Filed: Apr. 16, 2014

(65) Prior Publication Data

US 2014/0311090 A1   Oct. 23, 2014

(30) Foreign Application Priority Data

Apr. 19, 2013   (EP) .................................... 13164482

(51) Int. Cl.
| | | |
|---|---|---|
| *B65B 7/28* | (2006.01) | |
| *B67B 7/18* | (2006.01) | |
| *B67B 3/20* | (2006.01) | |
| *G01N 35/00* | (2006.01) | |
| *G01N 35/04* | (2006.01) | |

(52) U.S. Cl.
CPC ............... *B67B 7/182* (2013.01); *B67B 3/20* (2013.01); *G01N 35/0099* (2013.01); *G01N 2035/0405* (2013.01)

(58) Field of Classification Search
CPC . B67B 7/182; B67B 3/20; B25J 15/12; G01N 35/0099; G01N 2035/0405; B65B 7/2835
USPC ................. 53/331.5, 317; 279/2.01, 2.02, 50
See application file for complete search history.

(56) References Cited

U.S. PATENT DOCUMENTS

| | | | |
|---|---|---|---|
| 4,558,554 A | * | 12/1985 | Herbert ................. B67B 3/2073 53/317 |
| 5,417,031 A | | 5/1995 | Bankuty et al. |
| 5,983,596 A | | 11/1999 | Corniani et al. |
| 6,170,232 B1 | * | 1/2001 | VandeGeijn .......... B23B 31/113 279/4.09 |
| 6,398,281 B1 | * | 6/2002 | Heimberg .............. G01N 35/00 294/100 |
| 7,765,772 B2 | | 8/2010 | DeLuca et al. |
| 7,836,664 B2 | | 11/2010 | Zanini et al. |
| 8,458,992 B2 | | 6/2013 | Zanini et al. |
| 2007/0068117 A1 | | 3/2007 | Lang et al. |

(Continued)

FOREIGN PATENT DOCUMENTS

EP            2179758 B1    9/2013

*Primary Examiner* — Robert Long
*Assistant Examiner* — Xavier A Madison
(74) *Attorney, Agent, or Firm* — Standley Law Group LLP

(57) ABSTRACT

A rotatable gripper grips and turns a container cap. When locked, a collet clamp engages the cap, and when unlocked, the clamp releases the cap. The collet clamp is elongate with a first and second ends. The first end has a substantially rigid section. The second end has a gripper section with a substantially cylindrical recess that expands in width to hold the cap when the clamp is moved from locked to unlocked. Between the rigid and gripper sections is a clamping section. An outside surface of the clamping section is conical with a width increasing towards the gripper section. Sliding a ring on the conical clamping section deforms it into the locked position, constricting the recess tightly onto a container cap. When unlocked, the recess widens, permitting the cap to be removed from the recess.

12 Claims, 3 Drawing Sheets

(56) References Cited

U.S. PATENT DOCUMENTS

2009/0020530 A1* 1/2009 Baughman ........... B65D 39/082
                                                    220/288
2009/0247841 A1    10/2009 Werner et al.

* cited by examiner

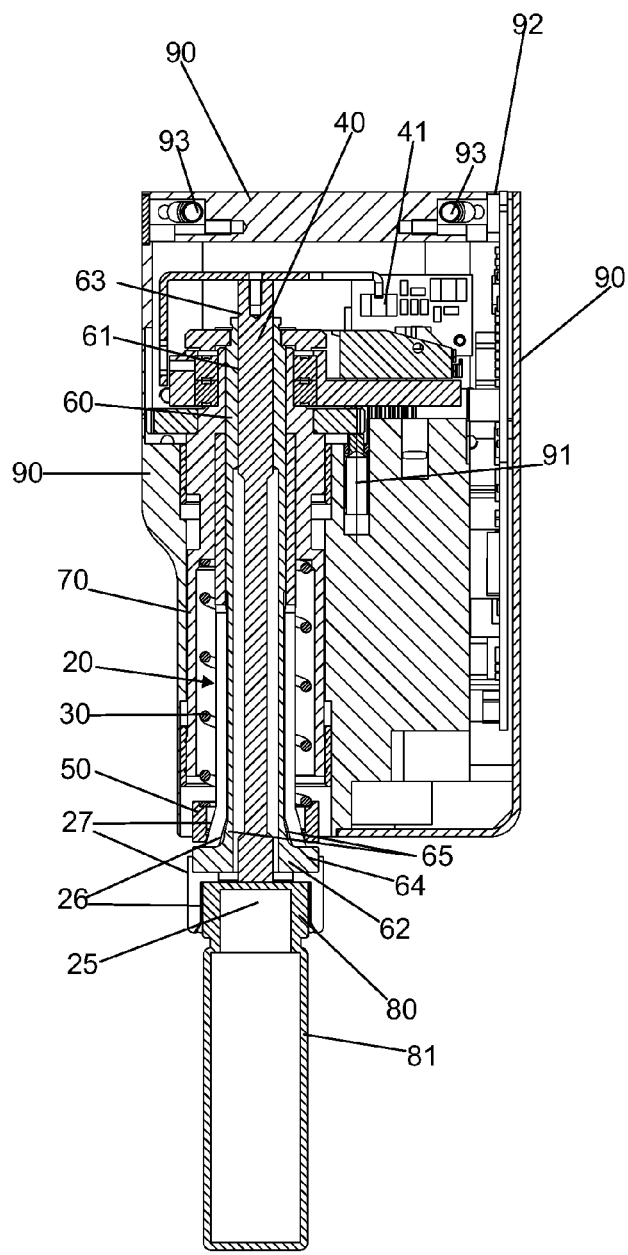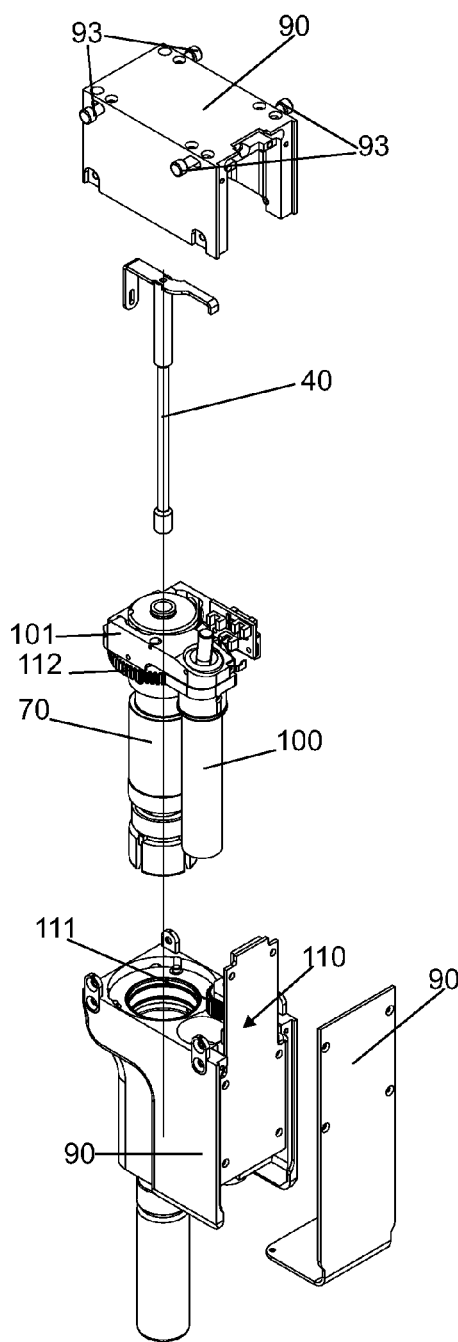
Fig. 2
Fig. 3

SAMPLE PREPARATION SYSTEM WITH ROTATABLE GRIPPER

CROSS-REFERENCE TO RELATED APPLICATIONS

This application is entitled to benefit of a right of priority under 35 USC §119 from European patent application 13164482.5, filed on 19 Apr. 2013, the content of which is incorporated by reference as if fully recited herein.

TECHNICAL FIELD

The present invention concerns a rotatable gripper which serves to open and close rotatable container caps. The rotatable gripper according to the invention is intended primarily for use in a sample preparation system.

BACKGROUND

The sample preparation system serves for the preparation of a large number of samples that are filled into containers. The empty containers are arranged in a sample rack. To perform the fill operation, an empty container which is closed with a screw cap is picked up with a tool and placed on a load receiver of a balance. Next, the cap is removed and the desired amount of the required substance is filled into the container, with the mass of the substance being measured by the balance. Then, the container is closed with the cap and returned to the sample rack.

This describes the operation in which a rotatable gripper is used. The rotatable gripper is parked in a base station. From there, the rotatable gripper is picked up by the robot arm and moved to the container that is to be fetched. The rotatable gripper takes hold of the container, and the robot arm moves the rotatable gripper with the container to the load receiver, where the container is set down. Next, the rotatable gripper opens the screw cap through a rotating action. Then, the rotating gripper with the cap is temporarily parked at the tool base station and the open container is filled with the desired substances. The filling is performed with a dosage-dispensing device, for example a dispensing head which contains or is connected to a supply of the substance. If the container is to be filled with a plurality of different substances, different dispensing devices will be used which are transported by the robot arm between the container and a dispensing device base station. After the filling process has been concluded, the rotating gripper is picked up again by the robot arm and moved to the container. The cap, which is still held by the rotating gripper, is screwed back onto the container, and the filled container is returned to the sample rack.

Typically, the sample amount dispensed into the container is in the range between 0.5 mg and 5000 mg. The weighing of such a small amount of mass requires a balance of high accuracy.

The sample preparation system is used in a laboratory environment. In the preparation of samples, critical substances are dispensed into a container. These substances must not be contaminated with lubricants.

The existing state of the art offers a variety of rotatable grippers.

Rotatable grippers that hold the cap by means of swivel jaws are disclosed in U.S. Pat. No. 7,836,664 B2, EP 2179758 B1, WO 2008043498 A1 and US 2007/0068117 A1. These rotatable grippers have the disadvantage that the jaws have to be greased with a lubricant, which can lead to contamination of the substances being dispensed. In addition, the jaws are pushed down on the cap by a spring force. Thus, the vertical force of the jaws bears against the cap and thus pushes down on the balance. As the balance is highly sensitive, it is therefore possible that the overload protection device of the balance is triggered, which can lead to a shift of the zero point of the balance. Subsequent measurements could thus be inaccurate.

Other rotatable grippers, which are disclosed in U.S. Pat. No. 7,765,772 B2 and U.S. Pat. No. 5,417,031 A, push down on the screw cap during the closing operation through the elastic force of a spring. This spring force would also act on the load receiver and trigger the overload safety device of the balance.

It is therefore the object of the present invention to provide a rotatable gripper which does not cause contamination and does not activate the overload safety device of the balance.

SUMMARY

This task is solved by the rotatable gripper according to the independent claim and the subordinate claims depending on it.

The rotatable gripper according to the invention is capable of gripping and turning a container cap. It is equipped with a rotatably supported collet clamp which has a locked operating position where the cap can be clamped in the collet and turned by the latter, and an unlocked operating position where the cap can be released from the collet. The collet clamp is of an elongate configuration, with a first and a second end. The first end comprises an essentially rigid section, while the second end comprises a gripper section with an essentially cylindrical recess that serves to hold the cap and can be expanded in width in the change from the locked to the unlocked operating position. In a preferred embodiment, the basic configuration of the cylindrical recess is circular. However, other configurations are also possible, such as for example triangular, quadrangular, or polygonal. According to the invention, a clamping section is arranged between the gripper section and the rigid section of the collet. The gripper section and the clamping section have an inside surface and an outside surface, wherein the outside surface of the clamping section has the shape of a cone whose width increases towards the gripping section and which is designed to be elastically deformable. The inside surface of the clamping section and the inside surface of the gripping section adjoin each other directly. The same applies to the outside surface of the clamping section and the outside surface of the gripping section. In the locked operating position, the deformable cone can be compressed by means of a ring that is slidably seated on the cone, whereby the recess can be compressed in such a way that a cap that is located in the recess can be clamped tightly. By loosening the ring, the recess can be made wider, so that the cap can be removed again from the recess. The ring is made of an essentially rigid material. The operating position of the collet clamp is essentially vertical. Accordingly, in the operating position the first end with the rigid section is located above the second end with the gripper section. The ring and cone are coaxial with the axis of the collet clamp. As the cone has a smoothly narrowing taper towards the clamping section and as the collet is oriented vertically, the ring is pushed by gravity onto the cone and thereby constricts the recess in the gripper section. Thus, the container cap is locked into the gripper section of the collet clamp. When the ring is moved upwards, the pressure on the cone is released and the recess in the gripper section expands, so that the cap can be removed from the gripper section.

The rotating gripper according to the invention has the advantage that no lubricant needs to be used between the ring and the cone. Thus, the sample substance cannot be contaminated by lubricant.

As a further advantage of the invention, the cap is locked into the recess by the ring sitting on the cone. No additional force is acting on the load receiver, and the overload safety device of the balance is not being triggered.

The ring is preferably held on the cone in the locked operating position by means of a spring that coaxially surrounds the collet clamp. As a result of this arrangement, the spring force is acting likewise in the vertical direction, and the spring occupies for the most part the space around the clamping section of the collet. The spring force is designed to be sufficiently large to hold the ring in place in the locked operating position. The locked operating position is maintained only by the pre-tensioning force of the spring. To change to the unlocked operating position, the spring needs to be compressed further. Thus, the locked state of the ring is a passively occurring condition. To be released, the ring has to be pushed up by an active force against the opposition of the spring force. The ring can be retracted from the cone by means of a retractor rod against the force of the pre-tensioned spring in order to attain the unlocked operating position. Alternative embodiments can have a hydraulically or pneumatically operated mechanism acting in conjunction with a rotary clutch.

The retractor rod is essentially of an elongate shape and is arranged in a hollow space inside the collet clamp. The retractor rod has a first and a second end. The first end is arranged essentially at the height of the ring. The first end has fingers which can reach through cutouts of the gripper section and are configured so that the ring is raised up when the retractor rod is moved upwards and the collet clamp can take its unlocked position. In the locked position, neither the retractor rod nor the fingers are touching the ring and the collet clamp. The spring force does not act on the load receiver in either the locked or the unlocked operating position, which assures that the overload safety device of the balance is not being triggered.

The second end of the retractor rod is arranged inside the collet clamp. A driving mechanism engaging the second end serves to raise and lower the retractor rod and thus serves to control the switching between the unlocked and the locked operating position.

The move to the unlocked operating position is facilitated by the fact that the inside surface of the collet clamp has an upwardly narrowing conical taper and the retractor rod has a conical, upwardly narrowing tapered section which cooperates with the conical inside surface of the collet clamp in such a way that in the change from the locked to the unlocked operating position the width of the recess is expanded by the spreading-apart of the gripper section of the collet clamp. The collet clamp is constructed advantageously of a material that springs back easily after deformation. It is important for the collet clamp to have springlike resilience in the radial direction, which can be significantly enhanced by lengthwise directed kerf slits which are arranged in the clamping section and in the gripper section. Ideally, the slits run out open-ended in the axial direction at the end of the collet clamp in the gripper section. This makes it easier to compress the gripper section. In the unlocked operating position, the collet clamp is free of elastic tension. In the locked operating position, the collet clamp is in a state of spring tension. Due to material fatigue it is possible that the elastic resilience may decrease over the life of the collet clamp. To ensure that the collet clamp can still be released, the conical or upwardly narrowing section of the retractor rod and the conical inside surface of the gripper section cooperate in the manner described above. This action can also be described as a forced opening of the collet clamp. This feature is most effective if the two conical surfaces run essentially parallel to each other.

In an alternative embodiment, the collet clamp is made of a material without elastic spring properties. In such a design, the collet clamp is always spread apart by the cone of the retractor rod in order to attain the unlocked operating position.

With preference the collet clamp and the ring are arranged in a sleeve, wherein the collet clamp is solidly connected to the sleeve. The connection between the sleeve and the collet clamp can be achieved with a form-locking or force-based engagement of the two parts. Advantageously, the collet clamp, the ring and the sleeve are arranged coaxially. The sleeve is preferably of a concentric design and rotatably supported in a housing. Due to the concentric configuration, the circular ring can be enclosed by the sleeve with a precise fit.

When the cap is opened or closed, the screw thread of the cap will cause the latter to move, respectively, up or down over a height difference of typically about 8 millimeters. This vertical movement of the cap and of the collet clamp holding the cap can cause the collet to become misaligned in the housing. This tendency can be counteracted with a design where the sleeve in its operating position is supported in the housing with vertical mobility. This arrangement offers the advantage that the sleeve with all of the components arranged inside it is moved up and down together with the cap. The problem of the collet clamp getting out of alignment in the housing is thereby avoided.

The rotatable gripper according to the invention includes a first drive mechanism to raise the ring and a second drive mechanism to rotate the collet clamp. Advantageously, the first as well as the second drive mechanism are arranged laterally of the collet clamp. This arrangement offers the advantage that the rotatable gripper has a compact design. The compact configuration is especially advantageous if the rotatable gripper is used with a robot arm. In rotatable grippers of the prior art, for example EP 0876991 B1, the drive mechanism is arranged above the collet clamp. These known rotatable grippers do not need to be moved as they are firmly installed. However, these embodiments of the state of the art have the disadvantage that the rotatable gripper is too tall. Consequently, the robot arm would require more room, the transfer distances would be longer, and a larger space would be needed to store the rotatable gripper. As a consequence of their design configuration, rotatable grippers of the existing state of the art have the further disadvantage that the force transmission levers would be larger. A larger lever ratio, in turn, could cause inaccuracies, which can have a big influence especially in critical laboratory applications.

Advantageously, in the operating state of the rotatable gripper, the first drive mechanism generates a movement in the vertical direction. This vertical movement raises the ring by way of a lever and the retractor rod. The lever has a first end and a second end. The first end of the lever is connected to the first drive mechanism, and the second end of the lever is connected to the retractor rod by way of a guiding system. The guiding system is configured in such a way that the rotary movement of the lever is converted by two movably supported guide pins into a purely vertical movement of the retractor rod. Advantageously, a ball joint is arranged between the lever and the first drive mechanism, wherein the ball joint transmits a rotary movement to the retractor rod. Due to this arrangement, the first drive mechanism can remain in the same position; only the lever is tilted, and the ball joint prevents jamming of the sleeve during the vertical movement.

The second drive mechanism preferably moves a drive gear which, in the operating state, is oriented horizontally and is arranged to cooperate with a collet gear that is connected to the sleeve. The drive gear is designed thicker than the collet gear, so that the latter will remain in mesh with the drive gear also when the collet moves up or down. The vertical height of the drive gear is selected so that the collet gear can mesh with the drive gear when the cap is completely screwed on as well as when it is completely screwed off. The drive mechanism together with the rotatable gripper is mounted so that it stays in a fixed position during the opening and closing action. The collet is supported with vertical mobility in the rotatable gripper. Consequently, the drive mechanism is able to move vertically in relation to the collet.

It is advantageous if the collet clamp is supported in a floating condition by means of a vertically oriented housing spring which is arranged between the housing and the collet clamp, wherein in the operating state the collet clamp is pushed downward against the spring force of the housing spring. When the collet clamp is used on a balance of high precision it is important that the balance is never exposed to the entire weight of the rotating gripper whereby the overload safety device could be triggered. When the collet clamp is moved downward against the spring force of the housing spring as a result of the rotation of the screw cap, the collet clamp springs back up after the clamping section is released. This ensures that the weight of the collet clamp never rests on the balance. During this operation, the housing spring is typically compressed by about 2 millimeters.

The retractor rod advantageously has a central bore hole for a sensor pin which is seated in such a way in the passage that the sensor pin is pushed upwards along the axis of the central bore hole when a cap is present in the recess. This displacement can be detected by means of a suitable sensor, and a corresponding signal can be transmitted to the user or to a computer system. Typically, an optical sensor with a light gate is used for this purpose, but other sensors could also be considered.

Ideally, the collet clamp and the ring are made of anodized and/or PTFE-coated aluminum (PTFE=polytetrafluoroethylene, commonly known as Teflon™). Other parts such as for example the sleeve can also be made of the same materials, which offer the advantage of having a smooth surface and thus a small coefficient of friction. Due to the low friction between the components it is unnecessary to add lubricants which could lead to contamination of the substances being filled into the containers. As a further advantage, there is less friction between the components of the rotatable gripper according to the invention. Consequently, the rotatable gripper is less susceptible to wear.

BRIEF DESCRIPTION OF THE DRAWINGS

Details of the rotatable gripper are presented in the description of an embodiment which is illustrated in the drawings, wherein identical parts are identified with identical part numbers and wherein:

FIG. 2 shows a sectional view of embodiment of the rotatable gripper;

FIG. 3 shows an exploded view of the embodiment of the rotatable gripper; and

DETAILED DESCRIPTION

Figure 1:
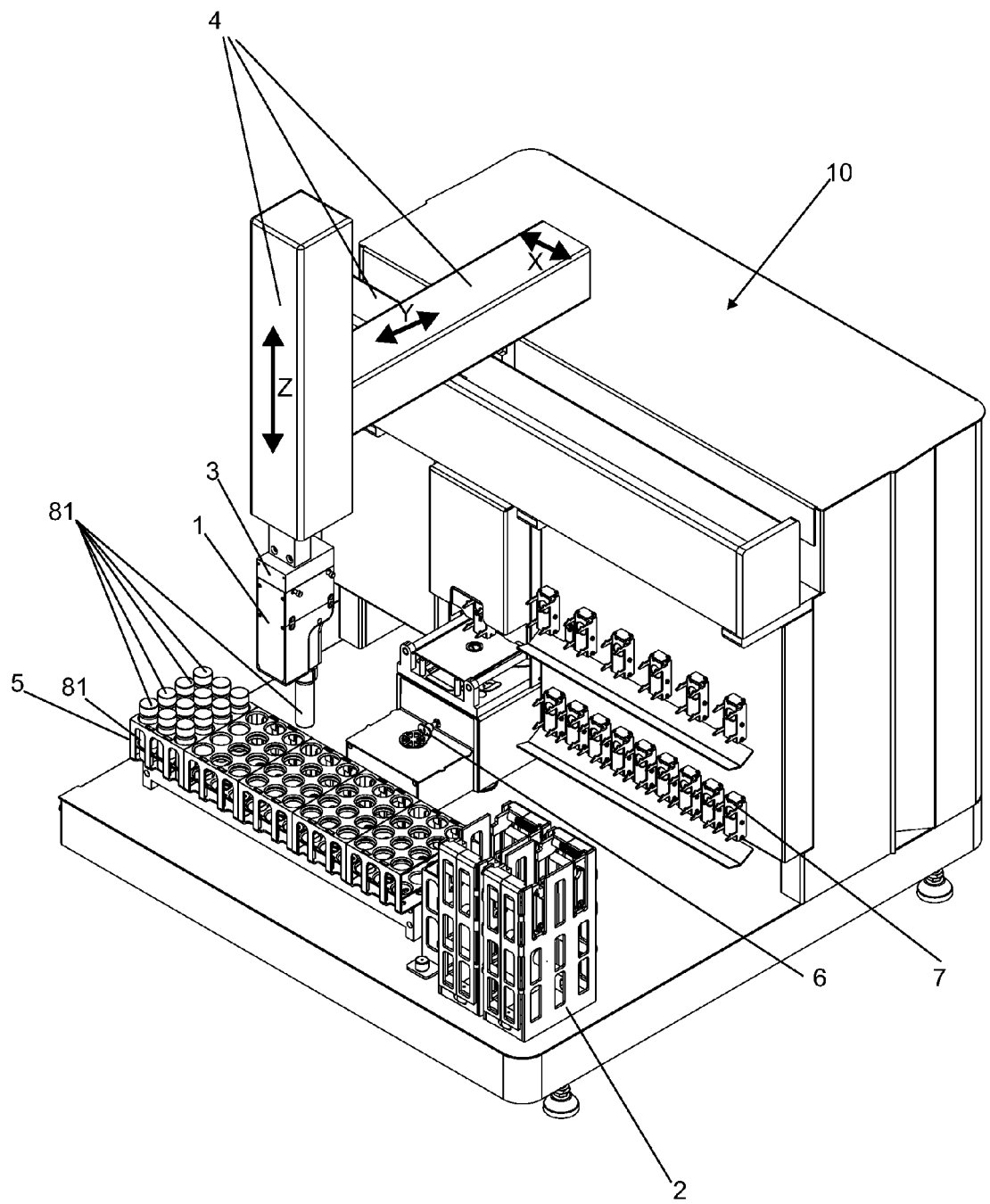
FIG. 1 shows a sample preparation system in which an embodiment of the rotatable gripper is employed.

FIG. 1 shows a sample preparation system 10 in which the rotatable gripper 1 according to the invention is employed for the preparation of samples. The sample preparation system 10 includes a tool base station 2 in which a variety of tools, such as for example the rotatable gripper 1 or a gripper for a powder-dispensing head, are parked temporarily. A sample rack 5 holds a plurality of containers 81. In the storage rack 7 for dosage-dispensing heads, different materials contained in individual dispensing heads can be kept ready for use. When samples are to be prepared, containers 81 can be placed on the load receiver 6. The motion module 4 allows the tool holder 3 to be moved in the x-, y- and z-directions.

To begin the preparation of a sample, the tool holder 3 is moved by means of the motion module 4 to the tool base station 2, where the tool holder 3 receives the rotatable gripper 1. A closed empty container 81 is taken out of the sample rack 5 and placed on the load receiver 6 by means of the rotatable gripper 1, where the cap 80 is removed from the container 81 by means of the rotatable gripper 1. After the cap 80 has been removed, the rotatable gripper 1 together with the cap 80 is parked in the tool base station 2. Next, the prescribed substances are dispensed into the open container 81, as the masses of the dispensed substances are monitored and the dispensing operation is controlled by means of a balance which is connected to the load receiver 6. After the desired substances have been filled into the container 81, the tool holder 3 picks up the rotatable gripper 1 containing the cap 80, closes the container 81 on the load receiver 6 with the cap 80 held in the rotatable gripper 1, and then moves the closed container 81 back to the sample rack 5. Subsequently, further containers 81 are filled with the prescribed substances, if desired.

FIG. 2 shows a sectional view of the rotatable gripper 1 according to the invention with a closed container 81 held by the collet clamp 20. The same components are also illustrated in FIG. 3 in an exploded view.

The rotatable gripper 1 includes a housing 90 containing the collet clamp 20 and the drive mechanisms 100, 110 through which the collet clamp 20 is actuated. The housing 90 has side walls and a cover plate. In the operating state, the cover plate is essentially horizontal and located above the collet clamp 20. Arranged on the cover plate are elements for the attachment of the housing 90 to the tool holder 3. These elements can be configured as pins 93, but other configurations are also conceivable. Also arranged on the housing 90 is an electrical connection 92 through which the rotatable gripper 1 is supplied with electrical power and/or data signals from the tool holder 3 to power and control the drive mechanisms 100, 110. The collet clamp 20 which is inside the housing 90 has a first and a second end and is of an elongate configuration. In the operating state the longitudinal axis of the collet clamp 20 is essentially vertical. The first end of the collet clamp 20 comprises an essentially rigid section 21. The second end comprises the gripper section 22 which has an essentially cylindrical recess 25 that serves to hold the cap 80. The gripper section 22 can be spread open or tightened, whereby the recess 25 is expanded or constricted. The constricted condition of the recess 25 corresponds to the locked operating position where a cap 80 can be held tight in the gripper section 22 and turned by it. The spread-open condition of the recess 25 corresponds to the unlocked operating position where the cap 80 can be released from the gripper section 22. A clamping section 23 is arranged between the rigid section 21 and the gripper section 22. By way of the clamping section 23 the gripper section 22 can be tightened and loosened. The tightening and loosening is achieved through an outside surface 27 of the clamping section 23 which at least in part has the shape of a cone 24 whose width increases towards the gripping section 22. The cone 24 is designed to be elastically deformable in the radial direction, i.e. to have radial flexibility. The gripper section 22 and the clamping section 23 are designed so that compressing the cone 24 causes a constriction of the recess 25, putting the rotatable gripper into the locked operating position. Expanding the cone causes a widening of the recess 25, putting the rotatable gripper into the unlocked operating position. An essentially rigid ring 50 which can slide up and down is resting on the flexible cone 24. Pushing the ring 50 downward in the operating position causes the cone 24, and consequently the recess 25, to be constricted, putting the rotatable gripper into the locked operating position. On the other hand, moving the ring 50 upward causes the cone 24, and consequently the recess 25, to expand, putting the rotatable gripper into the unlocked operating position. The geometry and the material for the collet clamp 20 are selected so that the latter is clamped tightly in the locked operating position and released in the unlocked operating position. Thus, pushing the ring 50 onto the cone 24 has the effect of compressing the cone 24. Retracting the ring 50 allows the tension in the material of the collet clamp 20 to relax so that the recess opens up.

The ring 50 is pushed onto the cone 24 by a pre-tensioned spring 30. The spring 30 is arranged coaxially around the collet clamp 20. To allow the rotatable gripper to take on the unlocked operating position, the ring 50 has to be pushed upwards against the spring force of the spring 30. The spring force is stronger in the released position than in the locked position. To put the gripper into the released position, the ring 50 has to be actively pushed upward. This action occurs by way of a retractor rod 60. The retractor rod 60 has a first end 62 and a second end 63. The retractor rod 60 is arranged in a hollow space inside the collet clamp 20. The retractor rod 60 has a first end 62 and a second end 63. The first end 62 has fingers 64 which reach through slits 28 that are arranged in the gripper section 22 and clamping section 23. When the retractor rod 60 is moved upwards the ring 50 is pushed up against the pre-tensioning force of the spring 30. To ensure that the recess 25 will open up even as the material of the collet clamp 20 loses some of its elasticity over time, the inside surface 26 of the collet clamp 20 has an upwardly narrowing conical section 24 which cooperates with the upwardly narrowing conical surface 65 of the retractor rod 60 in such a way that when the retractor rod is moved upward the gripper section 22 is spread apart.

The second end 63 of the retractor rod 60 is arranged inside the rotatable gripper 1 and connected to a first drive mechanism 100. The first drive mechanism 100 moves the retractor rod 60 up and down in a controlled manner. The first drive mechanism 100 is arranged to the side of the retractor rod 60 and the collet clamp 20. The first drive mechanism 100 generates a rotary movement in a horizontal plane relative to the operating state of the rotatable gripper. This rotary movement is converted into a vertical movement by means of a ball joint 102 and a lever 101 which moves the retractor rod 60, and consequently also the ring 50, up and down relative to the normal operating position.

The collet clamp 20, the retractor rod 60 and the ring 50 are arranged inside a sleeve 70. The rigid section 21 of the collet clamp 20 is solidly connected to the sleeve 70. Ideally, the collet clamp 20 as well as the sleeve 70 are for the most part of rotationally symmetric configuration. The collet clamp 20, the ring 50 and the sleeve 70 are arranged coaxially with one another. The sleeve 70 is rotationally symmetric and rotatably supported in the housing 90. Due to the solid connection between the collet clamp 20 and the sleeve 70, the collet clamp 20 and the sleeve turn together. The container cap 80 is opened by rotating the sleeve 70 with the collet clamp 20 holding the cap 80.

Screwing the cap 80 onto or off the container causes the collet clamp 20, and consequently also the sleeve 70 with the components contained in it, to move, respectively, downwards or upwards. To take up this vertical displacement, the sleeve 70 is held in the housing 90 through a floating kind of suspension. The first drive mechanism 100 is supported in the housing 90 in a floating arrangement together with the collet clamp 20. To prevent the collet clamp 20 or the drive mechanism from becoming misaligned, a lever 101 which is rotatable about a horizontal fulcrum axis is arranged between the first drive mechanism 100 and the collet clamp 20. As an alternative, one could also use a rigid linear guiding constraint instead of the rotatable lever.

The rotary movement that is needed to open and close the cap 80 is generated by means of a second drive mechanism 110. The second drive mechanism 110 is likewise arranged to the side of the collet clamp 20. Due to this lateral arrangement, a compact design of the rotatable gripper 1 is achieved. The second drive mechanism 110 acts through a drive gear 111 extending horizontally in the operating state. This drive gear 111 meshes with a collet gear 112 that is connected to the sleeve 70. Rotation of the drive gear 111 turns the collet gear 112, whereby a cap 80 clamped in the collet 20 is screwed onto, or unscrewed from, the container 80. The second drive mechanism 110 is solidly connected to the housing, which means that the second drive mechanism 110 does not move up or down together with the cap 80. To ensure that the two gears 111, 112 mesh with each other in any position, the drive gear 111 is designed thicker than the collet gear 112. It is also possible that the collet gear is designed thicker than the drive gear 111.

Between the collet clamp 20 and the housing 90, a vertically oriented housing spring 91 is arranged in such a way that in the operating state the collet clamp 20 has to be pressed downward against the spring force of the housing spring 91.

The retractor rod 60 has a central bore hole 61 for a sensor pin 40 arranged in such a way that the sensor pin 40 is pushed upwards along the axis of the central bore hole when a cap 80 is present in the recess 25. This displacement can be detected by means of a suitable sensor, and a corresponding signal can be transmitted to the user or to a computer system. An optical sensor 41 with a light gate is used for this purpose, but other sensors could also be considered.

Figure 4:
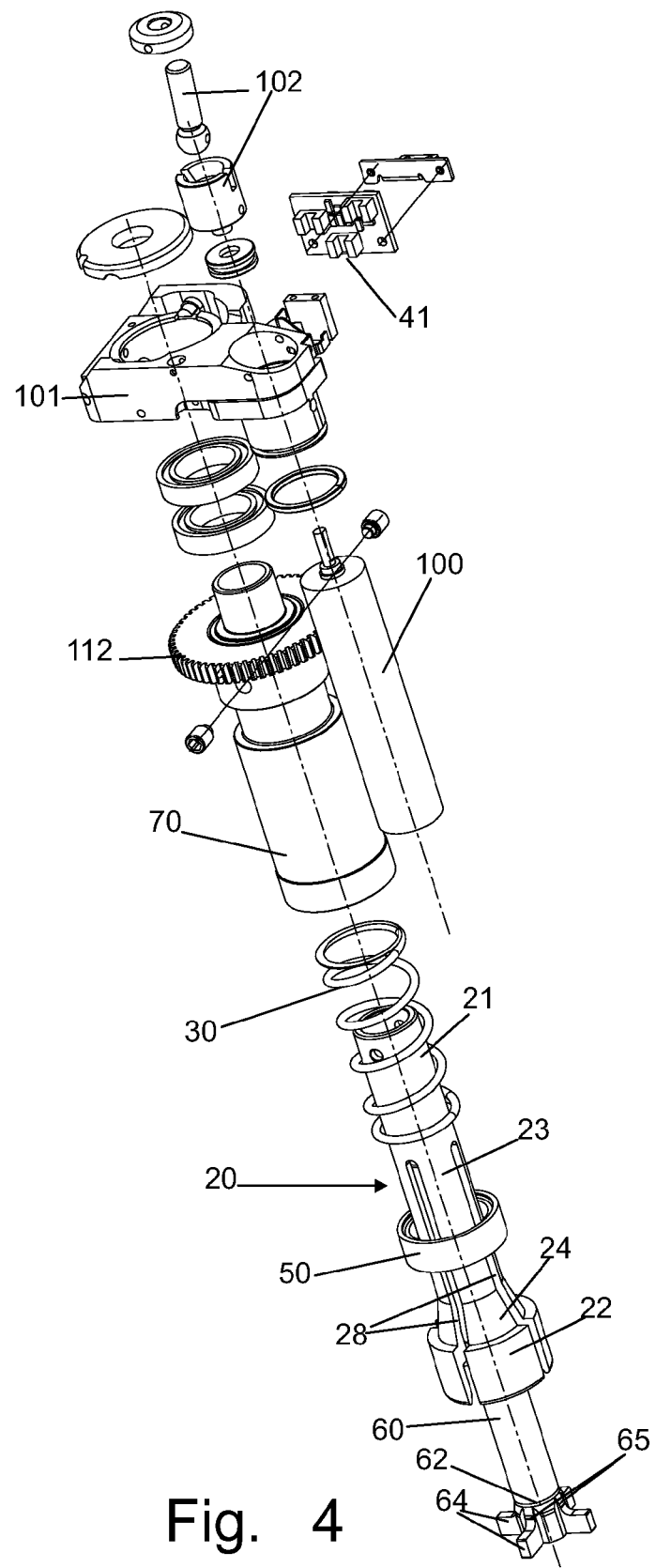
FIG. 4 shows an exploded view of the collet clamp.

FIG. 4 shows an exploded view of the collet clamp 20 of the rotatable gripper 1 according to the invention. The exploded view serves to more clearly illustrate the function of the collet clamp shown in FIGS. 2 and 3.

Although the invention has been described through the presentation of a specific embodiment, it is evident that numerous further variant versions could be created based on the teachings of the present invention.

What is claimed is:

1. A device for gripping and turning a cap of a container, comprising:
    a collet clamp, mounted for rotation, the collet clamp having a locked operating position and an unlocked operating position, the collet clamp having an elongate configuration with a first and a second end, and an inside surface with a conical shape that narrows in the direction of the first end, comprising:
        a substantially rigid section, at the first end of the collet clamp;
        a gripper section, at the second end of the collet clamp, the gripper section having a substantially cylindrical recess on the inside surface of the collet clamp, the recess sized to hold a cap located therein when in the locked operating position;
        a clamping section, arranged between the gripper section and the rigid section, an outside surface of the collet clamp at the clamping section having a deformable conical shape with a width that increases towards the gripper section;
    a ring, slidably positioned on the clamping section, so that, in the locked operating position, the ring deforms the deformable conical shape, constricting the recess of the gripper section and tightly clamping the cap, and, in the unlocked operating position, the recess widens so that the cap can be removed therefrom;
    a spring, arranged to coaxially surround the collet clamp and push the ring against the deformable conical shape when the collet clamp is in the locked operating position; and
    a retractor rod, arranged inside the collet clamp to move the ring away from the conical shape against the force of the spring, moving the collet clamp to the unlocked operating position, wherein the retractor rod has at least one tapered section of decreasing diameter in the direction of the first end of the collet clamp, the tapered section cooperating with the conical inside surface such that the recess is enlarged by the spreading-apart of the gripper section when the operating position is changed from locked to unlocked.

2. The device of claim 1, further comprising:
    a sleeve, in which the ring and the collet clamp are arranged, the collet clamp being solidly connected thereto.

3. The device of claim 2, wherein:
    the collet clamp, the ring and the sleeve are arranged coaxially with one another.

4. The device of claim 2, further comprising:
    a housing, in which the sleeve, having a rotationally symmetric design, is rotatably supported.

5. The device of claim 4, wherein:
    in an operating state of the device, the sleeve is vertically slidable in the housing.

6. The device of claim 5, further comprising:
    a first drive mechanism, operatively arranged for raising the ring; and
    a second drive mechanism, operatively arranged for rotating the collet clamp, each of the respective drive mechanisms arranged laterally of the collet clamp.

7. The device of claim 6, wherein:
    a lever and the retractor rod raise the ring though a movement in the vertical direction generated by the first drive mechanism.

8. The device of claim 7, further comprising:
    a ball joint, arranged between the lever and the first drive mechanism to transmit a rotary movement to the retractor rod.

9. The device of claim 6, further comprising:
    a drive gear, driven by the second drive mechanism and extending horizontally in the operating state of the device; and
    a collet gear, connected to the sleeve and arranged to mesh with the drive gear, the drive gear being thicker than the collet gear to remain meshed therewith as the collet clamp moves in the vertical direction.

10. The device of claim 4, wherein:
    a housing spring, oriented vertically in the operating state of the device, arranged between the housing and the collet clamp, such that an upward spring force of the housing spring supports the collet clamp in a floating condition.

11. The device of claim 1, further comprising:
    a sensor;
    a sensor pin; and
    a central bore hole in the retractor rod, in which the sensor pin is seated, so that the presence of a cap of a container in the recess displaces the sensor pin vertically along an axis of the central bore hole, the vertical displacement being detectable by the sensor.

12. The device of claim 1, wherein:
    the collet clamp and the ring are made of aluminum that is at least one of: anodized and coated with polytetrafluoroethylene.

* * * * *